(12) United States Patent  (10) Patent No.: US 6,517,561 B1
Phillips  (45) Date of Patent: Feb. 11, 2003

(54) MOTORIZED SPECIMEN CUTTER

(76) Inventor: Robert E. Phillips, 5256 Mission Rd., Suite 708, Bonsall, CA (US) 92003

( * ) Notice: Subject to any disclaimer, the term of this patent is extended or adjusted under 35 U.S.C. 154(b) by 0 days.

(21) Appl. No.: 09/962,016

(22) Filed: Sep. 25, 2001

Related U.S. Application Data

(60) Provisional application No. 60/239,975, filed on Oct. 16, 2000.

(51) Int. Cl.[7] ............................................... A61B 17/32
(52) U.S. Cl. ............................ 606/180; 600/567; 408/8
(58) Field of Search .................... 606/180, 179; 600/566, 567; 30/362; 408/8, 9, 68

(56) References Cited

U.S. PATENT DOCUMENTS 4,060,333 A * 11/1977 White .......................... 408/68
4,306,570 A * 12/1981 Matthews ................... 600/566
4,688,970 A *  8/1987 Eckman ......................... 408/9

* cited by examiner

*Primary Examiner*—Julian W. Woo
(74) *Attorney, Agent, or Firm*—Allen A Dicke, Jr.

(57) ABSTRACT

The motorized specimen cutter has a replaceable rotary tubular cutting tip and a motor to rotate the cutting tip. Deflection caused by proper cutting force energizes the motor with enough energy to cut a specimen. A manually or automatically actuated ejector pin ejects the sample from the cutting tip.

19 Claims, 4 Drawing Sheets

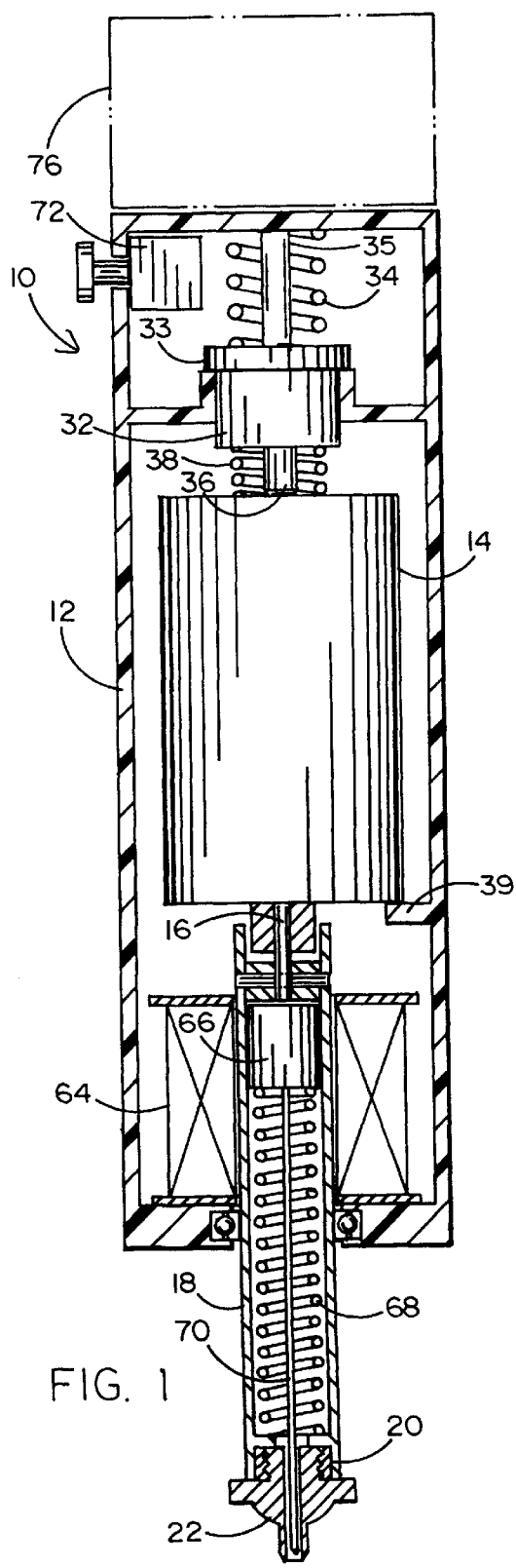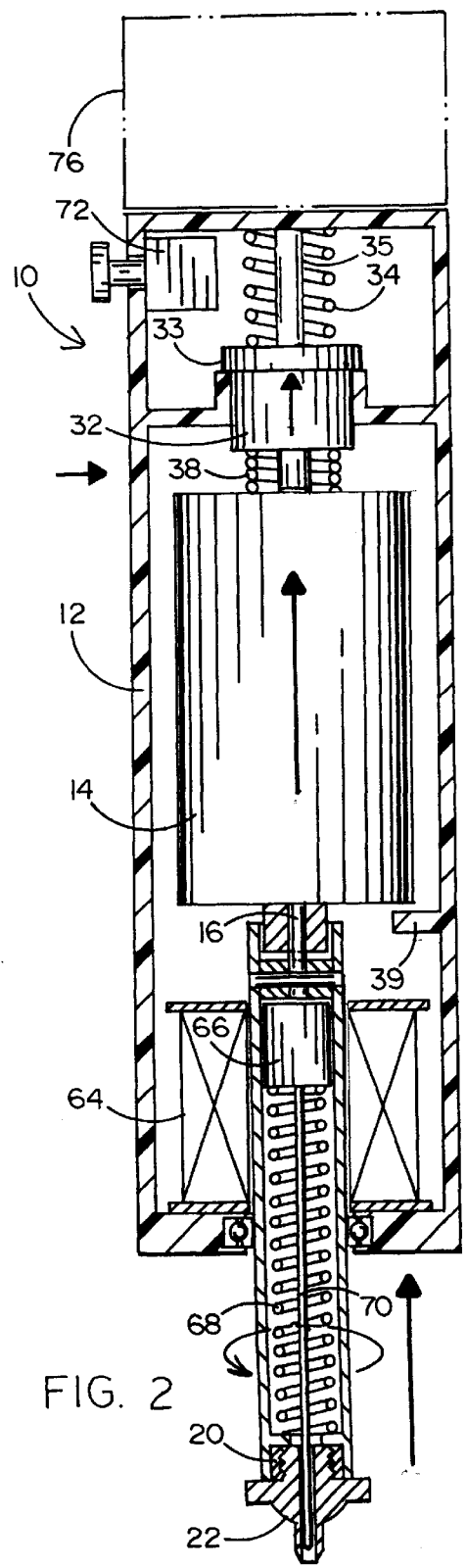
FIG. 1
FIG. 2

MOTORIZED SPECIMEN CUTTER

CROSS-REFERENCE

This application relies upon Provisional Application Ser. No. 60/239,975, filed Oct. 16, 2000, for priority.

FIELD OF THE INVENTION

This invention is directed to a hand-held motorized specimen cutter which is particularly useful in cutting and lifting specimens from FTA paper and lifting it off of the carrier medium.

BACKGROUND OF THE INVENTION

A particular paper which is used to retain a biological specimen is called "FTA paper." It is normally mounted upon a carrier which supports the FTA paper and protects the back of the FTA paper from contamination. When it is desired that the specimen be tested for particular biological materials, it is not usual to employ the, entire FTA paper, but cut a small sample therefrom. The cutting of such specimens is presently accomplished by using a cylindrical hollow tube cutter and manually rotating it against the paper. When the correct amount of force and rotation is employed, a disc of the FTA paper is cut and retained in the cutter tube. This cut is accomplished without cutting through the supporting and protecting backing layer. The proper manual technique is hard to learn and can only be learned through practice. Long-term manual rotation of the cutter by the technician is undesirable because it is potentially damaging to the hand, wrist and arm joints. A faster, less damaging and more reliable apparatus is required.

SUMMARY OF THE INVENTION

In order to aid in the understanding of this invention, it can be stated in summary form that it is directed to a specimen cutter which comprises a motor-rotated cylindrical tubular specimen cutter. The switch energizing the motor is preferably mounted such that the motor is only energized when the proper cutting force is achieved. The motor is only energized with sufficient energy to rotate the cutter enough to make a single cut. When the cutter is over-forced, it is deenergized.

It is, thus, a purpose and advantage of this invention to provide a specimen cutter which has a cylindrical tube rotating blade cutter which, on demand, is delivered just enough energy to cut a specimen without cutting into the backing layer.

It is a further purpose and advantage of this invention to provide a specimen cutter which is hand-held and which responds to force against the specimen sheet to start the cutting operation, and the cutting operation is provided only enough energy to cut through the specimen layer and not cut through the backing layer.

It is a further purpose and advantage of this invention to provide a specimen cutter which resiliently depresses when too much force is applied in the cutting direction.

It is a further purpose and advantage of this invention to provide a specimen cutter which will not cut through the backing layer when too much too much force is applied in the cutting direction.

It is a further purpose and advantage of this invention to provide a hand-held specimen cutter which is useful for application into an automatic specimen cutting machine so that specimens may be automatically cut and placed.

It is a further purpose and advantage of this invention to provide a hand-held specimen cutter which is controlled so that only the amount of energy is available to the motor to accomplish cutting out a specimen.

It is a further purpose and advantage of this invention to provide a specimen cutter which is adaptable to be used on a positioning machine so that the specimen cutter can semi-automatically cut and place specimens.

Other purposes and advantages of this invention will become apparent from a study of the following portion of the specification, the claims and the attached drawings.

BRIEF DESCRIPTION OF THE DRAWINGS

FIG. 1 is a side-elevational view of the specimen cutter, with the near half of some of the parts broken away and taken in section, shown in rest position.

FIG. 2 is a view similar to FIG. 1, but showing the specimen cutter in the act of cutting a specimen.

DESCRIPTION OF THE PREFERRED EMBODIMENT

Figure 3:
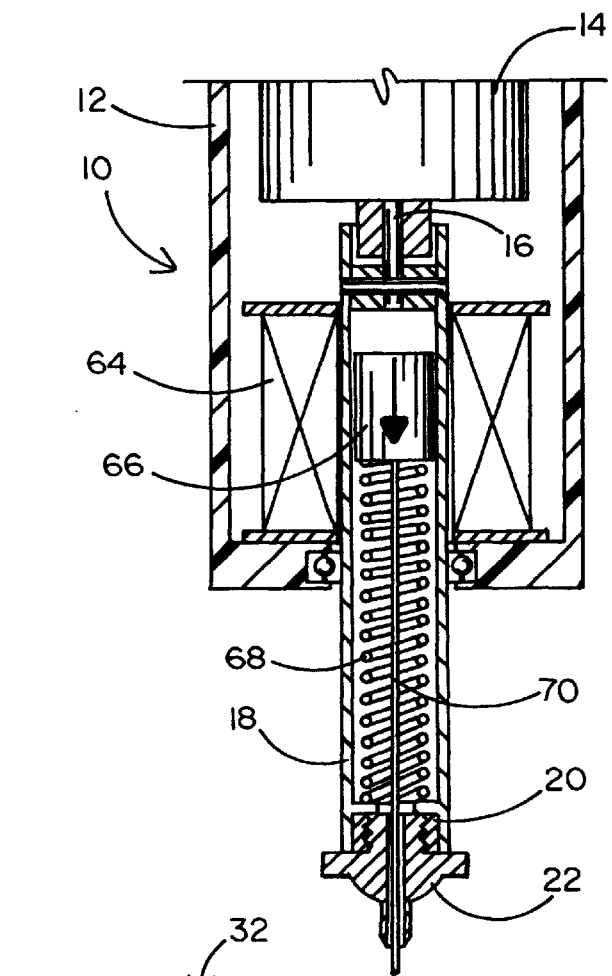
FIG. 3 is a partial view of the structure of FIG. 1, with the top portion broken away, and showing the specimen cutter ejecting the previously cut specimen.

The specimen cutter of this invention is generally indicated at 10 in FIGS. 1, 2 and 3. The specimen cutter 10 comprises a housing 12 which contains motor 14. The motor 14 has a rotatable output shaft 16 which is connected to rotate drive tube 18. Bushing 20 is secured in the lower end of the drive tube 18 and rotates therewith. Replaceable cutter head 22 is threaded into the bushing 20. The cutting tip 24 is seen in FIGS. 5, 6, 7 and 8. The motor 14 has a rotational axis on the axis of output shaft 16. The drive tube is a cylindrical tube which is driven by the motor to rotate on that axis. Bushing 20 and cutter head 22 are thus rotatably driven around that axis of rotation. The cutting tip 24 is a truncated cone with a cylindrical interior surface 26 to define a sharp edge on the cutting tip. The cutter head 22 is easily replaced by screwing a new one into bushing 20.

Figure 5:
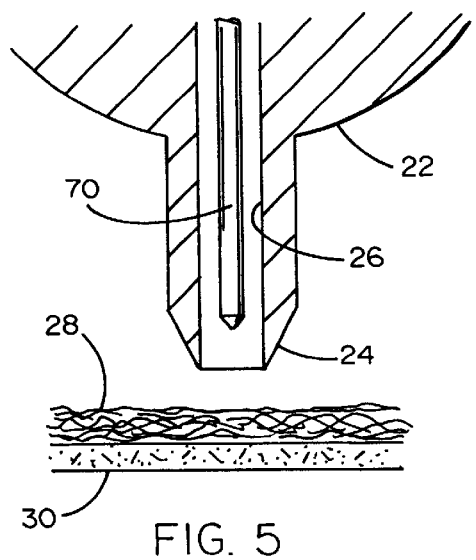
FIG. 5 is an enlarged detailed drawing showing the cutting tip adjacent the specimen carrier as the specimen cutter approaches the specimen carrier prior to cutting.
Figure 6:
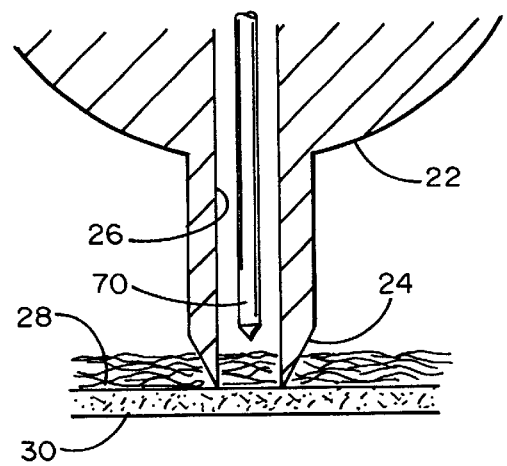
FIG. 6 is a similar viewing the completion and cutting.
Figure 7:
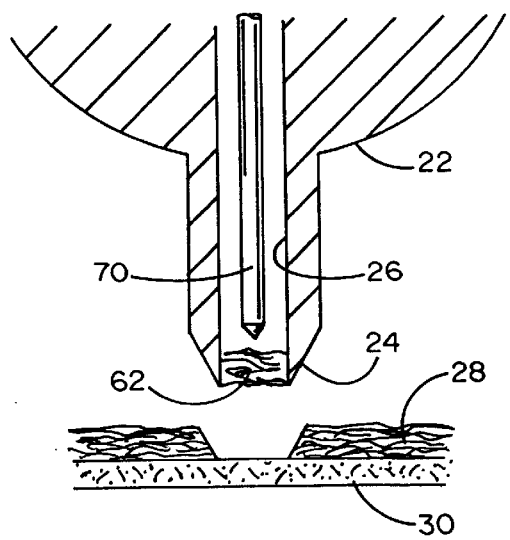
FIG. 7 is a similar view showing withdrawal of the specimen cutter carrying a specimen therewith.

FIGS. 5, 6 and 7 show a specimen carrier 28 which is supported by a backing layer 30. The specimen carrier is of a particular nature which stores biological samples, such as FTA paper, which is commonly used for blood samples. The backing layer 30 provides support for the specimen carrier layer and protects the under side of the specimen carrier layer from contamination. In the testing of biological specimens, only small portions of the sample are employed, so that repeat testing can be accomplished and some of the original material preserved.

Switch housing 32 is mounted in the housing 12 and is held downwardly by spring 34. Downward motion is limited by stop shoulder 33. Switch actuator 36 extends from switch housing 32 and almost contacts motor 14. Spring 38 holds the motor and the cutter head in a lower position against stop 39, as shown in FIG. 1. This is the approach position of the cutter head toward the specimen carrier 28, as shown in FIG. 5. In the preferred embodiment, the spring 38 is a light spring and represents the preferred force of the cutting tip against the specimen carrier. This spring compresses and the switch actuator 36 actuates switch 32 and the proper cutting force is achieved by the spring force. When switch 32 is actuated, the motor 14 is energized to rotate the cutter head 32 to cut out the specimen. This is seen in FIGS. 2 and 6.

Figure 4:
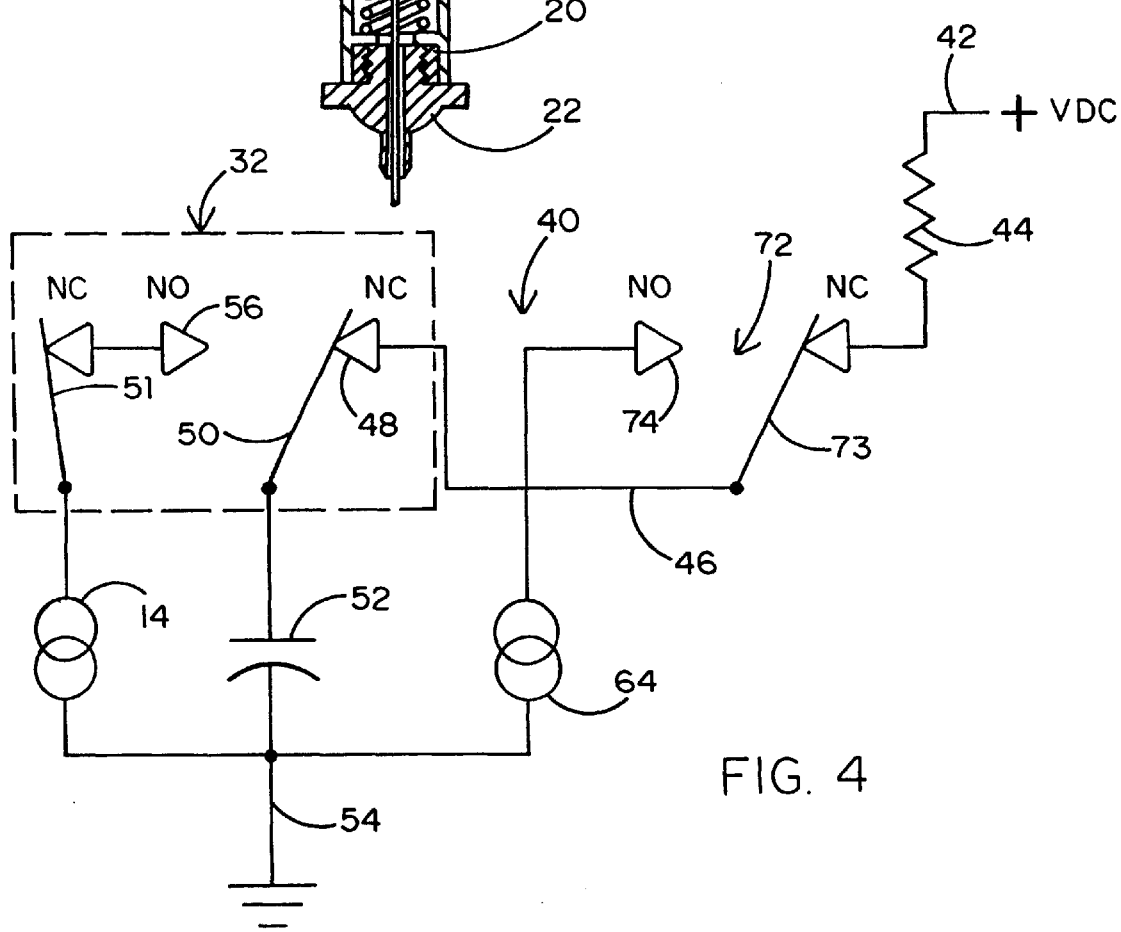
FIG. 4 is a simplified wiring diagram of the specimen cutter.

FIG. 4 is a schematic diagram of an electric circuit 40 which supplies power and other functions to the specimen carrier 10. DC voltage source 42 provides current through a limiting resistor 42 to line 45. Line 45 is connected to line 46 through switch 72. Switch blade 73 of switch 72 is in contact with the normally closed switch contact. Line 46 is connected to the normally closed contact 48 of switch 32. The switch blade 50 of the switch 32 is connected to capacitor 52, which has its other side connected to ground 54. The capacitor 52 becomes charged from the power supply. The normally open contact 56 is connected through switch blade 51 against its normally closed contact and through the windings of motor 14 to ground 54. Thus, when the rotating structure is pushed upward to move switch actuator 36 to move switchblade 50 in switch housing 32, as shown in FIGS. 2 and 6, the capacitor 52 is discharged through the motor 14.

The capacitor 52 has just enough energy in it to rotate the motor enough to do the proper cutting. Excess energy is not available so that the backing layer 30 is not cut through. This motor energisation is accomplished by the operator bringing the motorized specimen cutter 10 to the specimen carrier 28 and simply pressing it down. When the correct amount of force of the cutting tip against the specimen carrier 28 is achieved, the switch 32 is actuated and the correct amount of energy is supplied to the motor to do the cutting operation. If too much cutting force is applied, switch 32 moves upward against spring 34. This causes switch actuator 35 to depress into the switch housing 32. This action moves switchblade 51 away from its normally closed contact, see FIG. 4, which contact opening deenergizes motor 14 limiting the amount of force which can be applied to the cutting tip.

As the operator lifts the specimen cutter away, as seen in FIG. 7, it is necessary that he eject the specimen 62 from the tubular cutting tip. To accomplish this, magnetic coil 64 is mounted within the housing 12 adjacent its lower end and surrounding drive tube 18. Solenoid core 66 is mounted within the drive tube and is held upward by means of spring 68, as seen in FIGS. 1 and 2. Ejector rod 70 is mounted on the core and extends downward within the tubular cutter head. When the solenoid is not actuated, the tip of the ejector rod is above the cutting tip 24, as seen in FIGS. 5, 6, and 7. Energization of magnetic coil 64 and motion of the solenoid core and ejector rod is accomplished by manual operation of ejector switch 72, which is mounted high on the housing (see FIGS. 1 and 2).

Figure 8:
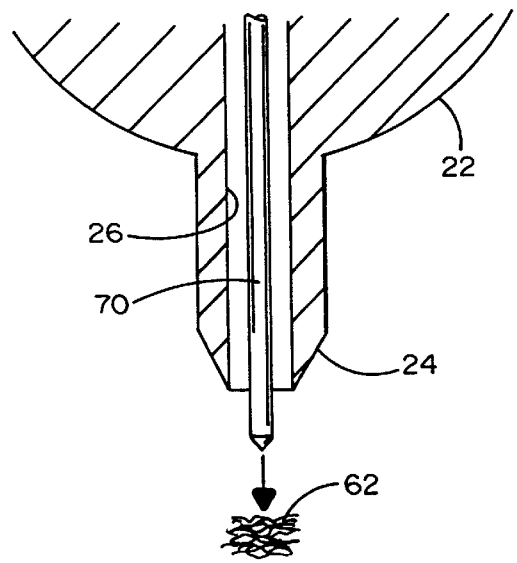
FIG. 8 is a similar view showing ejection of the specimen.

As seen in FIG. 4, switch 72 is normally closed but, when actuated, its switchblade 73 contacts normally open contact 74 to complete the circuit from the capacitor 52 to discharge the capacitor through the coil 64. This causes energization of the ejector solenoid. The downward motion of the ejector rod causes ejection of the cut specimen 62, as seen in FIG. 8. The power supply 42 can either be separate or in a battery pack 76, as shown in phantom lines in FIGS. 1 and 2. By this specimen cutter, manual skill and manual effort are replaced by the functions of the specimen cutter, which can be easily operated by lesser trained personnel.

Figure 9:
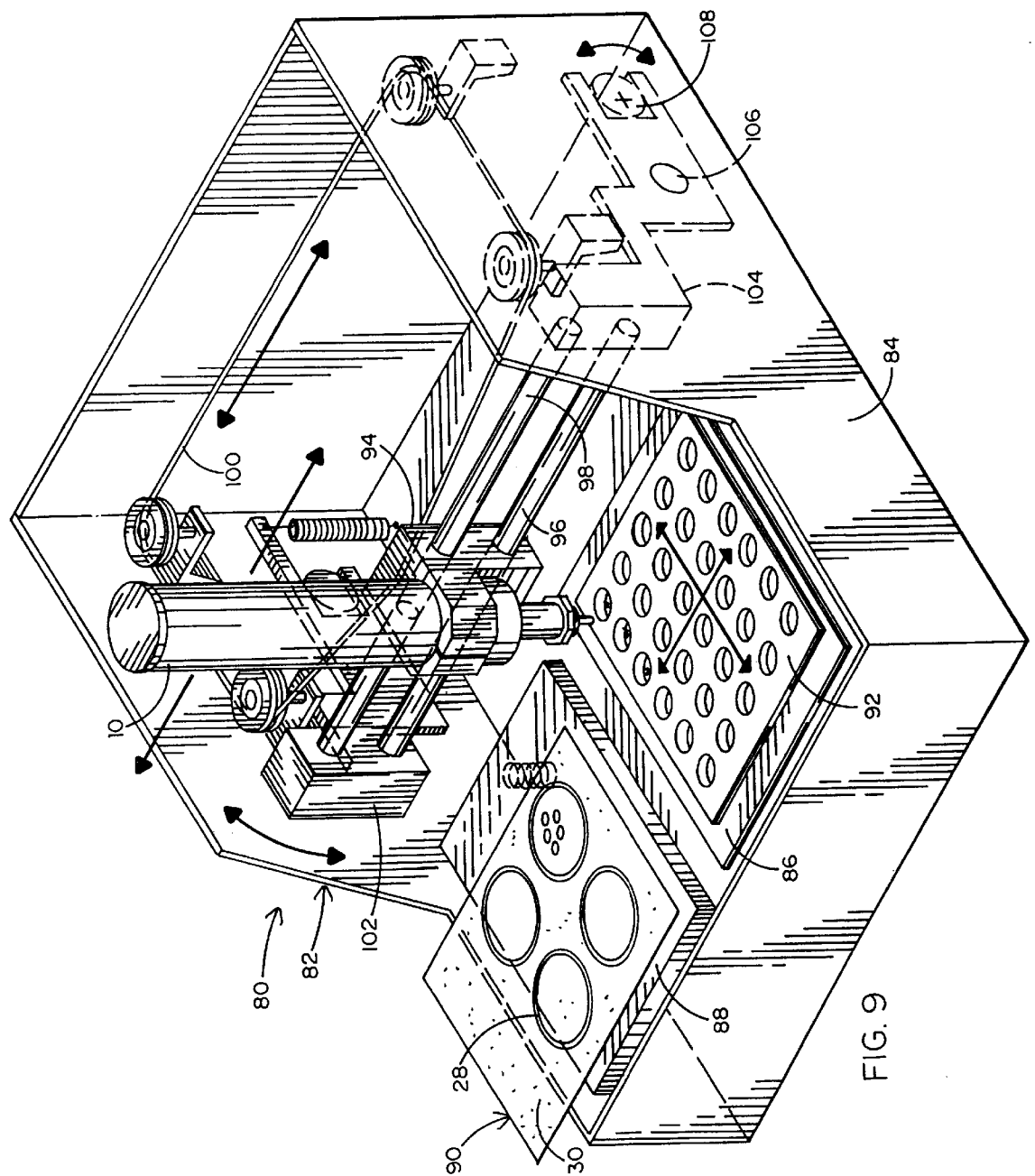
FIG. 9 is an isometric view of a positioning machine which utilizes the specimen cutter of this invention to semi-automatically cut and place specimens in a specimen tray.

The described motorized specimen cutter 20 is thus a suitable hand position motorized cutter. However, it is also feasible to use it as a portion of a semi-automated or fully automated specimen cutter system, such as the system 80 shown in FIG. 9. The system 80 comprises the specimen cutter 10 mounted on positioner 82. The positioner 82 has a frame 84 which carries a computer-positionable XY table 86. The frame also carries vacuum table 88 on which can be placed specimen sheet 90. The specimen sheet 90 comprises a backing layer 30 which may have one or more specimen coupons 62 thereon. The operator identifies the specimen coupon 62, perhaps by scanning a bar code into the system computer. The computer controls the XY table and identifies into which pocket of the tray 92 the cut specimen coupon goes. In this way, a continuous record of the specimen is maintained.

The specimen cutter 10 is actuated by pressing it down on the specimen. Thereupon, the specimen cutter is raised and is moved from a position over the specimen carrier 28 to a position over the tray 92 for deposit of the cut specimen. As one example of the mechanism which can move the specimen cutter with respect to the specimen carrier and tray, carriage 94 carries the specimen cutter therein. The carriage moves along guide bars 96 and 98 and is driven to the selected position by a computer-controlled positioning motor which drives band 100. Swing arms 102 and 104 are pivoted to rotate in the axis of pivot pin 106 and an aligned pivot pin on the left side of the frame. The rotation of the swing arms is controlled by eccentric 108, which is positioned by a motor controlled by the computer which keeps the system coordinated. The eccentric raises guide bars 96 and 98, which raise the specimen cutter 10. The specimen cutter is moved to the left over one of the specimen carriers 28, and the specimen cutter 10 is lowered to cut its specimen, as previously described. Thereupon, the specimen cutter 10 is raised and is moved over the tray 92. The tray is moved on its XY table to a position where the correct tray pocket is under the specimen cutter so that the specimen can be discharged. If desired, at this position the specimen cutter can again be lowered for closer positioning with respect to the pockets in the specimen tray. When appropriate, the specimen tray is removed from the positioner 82 and processed to determine the biological significance of the sample.

This invention has been described in its preferred embodiment, and it is clear that it is susceptible to numerous modifications and embodiments within the ability of those skilled in the art and within the scope of the following claims.

What is claimed is:

1. A specimen cutter comprising:
    a circular cutting tip for rotation about an axis for cutting a specimen out of a specimen sheet by rotation of said cutting tip and motion of said cutting tip axially toward a specimen sheet;
    an electric motor connected to said tip for rotating said tip;
    mounting structure for mounting said cutting tip within said specimen cutter to permit axial motion of said cutting tip with respect to said mounting structure in a direction away from the specimen sheet;
    a force device connected between said mounting structure and said cutting tip to urge said cutting tip axially in the cutting direction so that at a predetermined force, said cutting tip axially moves in a direction away from the specimen sheet; and a switch connected to said cutting tip and said mounting structure to be actuated by motion of said cutting tip with respect to said mounting structure, said switch being connected to said motor so that closure of said switch causes rotation of said cutting tip.

2. The specimen cutter of claim 1 wherein said motor is electrically connected to a limited energy source so that when said switch is actuated only sufficient energy to cause rotation of said cutting tip to cut one specimen is provided.

3. The specimen cutter of claim 2 wherein said cutting tip is mounted so that if more axial deflection of said cutting tip is caused than is necessary to actuate said switch, a second switch cuts off energization of the motor.

4. The specimen cutter of claim 1 wherein said cutting tip is removably mounted on said specimen cutter.

5. The specimen cutter of claim 1 wherein there is an ejector rod mounted within said cutting tip and there is an actuator to move said ejector rod axially out through said cutting tip to eject a specimen within said cutting tip.

6. The specimen cutter of claim 5 wherein said actuator is a second motor connected to said ejector rod and there is an electric switch connected to energize said second motor to cause motion of said ejector rod and ejection of a specimen.

7. The specimen cutter of claim 6 wherein said second motor is a solenoid with a plunger therein, said plunger being connected to said ejector rod.

8. The specimen cutter of claim 7 wherein there is a spring connected to said ejector rod to resiliently retain it in its first, non-ejector position so that when said solenoid is actuated said plunger moves against said spring to move said ejector rod out of said cutting tip.

9. The specimen cutter of claim 1 wherein there is a power supply connected to said motor, said power supply comprising a DC source and a capacitor connected to be charged by said DC source, said switch being connected so that when it is actuated, said capacitor is serially connected to said motor so that the energy delivered to said motor is limited substantially to the energy in said capacitor.

10. A specimen cutter system comprising:

a specimen cutter having a circular cutting tip for rotation about an axis for cutting a specimen out of a specimen sheet by rotation of said cutting tip and motion of said cutting tip axially toward a specimen sheet;

an electric motor connected to said tip for rotating said tip;

mounting structure for mounting said cutting tip within said specimen cutter to permit axial motion of said cutting tip with respect to said mounting structure in a direction away from the specimen sheet;

a force device connected between said mounting structure and said cutting tip to urge said cutting tip axially in the cutting direction so that at a predetermined force, said cutting tip axially moves in a direction away from the specimen sheet;

a switch connected to said cutting tip and said mounting structure to be actuated by motion of said cutting tip with respect to said mounting structure, said switch being connected to said motor so that closure of said switch causes rotation of said cutting tip; and a positioner, said specimen cutter being connected to and being positioned by said positioner.

11. The specimen cutter of claim 10 wherein said positioner comprises a specimen sheet table and a specimen tray table, said specimen cutter being movable from a position over said specimen sheet table for the cutting of a specimen from a specimen sheet thereon, to a position over said specimen tray table for depositing the cut specimen into a pocket in a specimen tray on said specimen tray table.

12. The specimen cutter of claim 11 wherein said positioner includes structure to raise and lower said specimen cutter with respect to said specimen sheet table and mechanism to move said specimen cutter over said specimen tray table.

13. A specimen cutter comprising:

a housing;

a tubular specimen cutter mounted with respect to said housing to rotate on an axis through said tubular cutter;

a motor mounted with respect to said housing, said motor being connected to rotate said tubular cutter;

a power supply connected to said motor to rotate said cutter, said power supply having sufficient power to rotate said cutter a sufficient amount to cut a specimen; and a force sensor connected to said cutter, said force sensor being connected to said power supply to connect said power supply to said motor when said force sensor detects sufficient force on said cutter to cut a specimen.

14. The specimen cutter of claim 13 wherein said force sensor is a resilient member which deflects when force is applied thereto and such deflection causes said power supply to be connected to said motor.

15. A specimen cutter comprising:

a housing;

a tubular specimen cutter mounted with respect to said housing to rotate on an axis through said tubular cutter;

a motor mounted with respect to said housing, said motor being connected to rotate said tubular cutter;

a power supply connected to said motor to rotate said cutter, said power supply having sufficient power to rotate said cutter a sufficient amount to cut a specimen; and a force sensor connected to said cutter, said force sensor being connected to disconnect power from said power supply to said motor when excessive force is sensed.

16. The specimen cutter of claim 15 wherein said force sensor is a resilient member which deflects when force is applied thereto and such deflection causes said power supply to be connected to said motor.

17. A specimen cutter comprising:

a housing;

a tubular specimen cutter mounted with respect to said housing to rotate on an axis through said tubular cutter;

a motor mounted with respect to said housing, said motor being connected to rotate said tubular cutter;

a power supply connected to said motor to rotate said cutter, said power supply having sufficient power to rotate said cutter a sufficient amount to cut a specimen;

a first force sensor connected to said tubular cutter, said first force sensor being connected to said power supply and to said: motor so that said power supply supplies power to said motor when adequate cutting force is sensed at said tubular cutter; and a second force sensor, said second force sensor being connected between said power supply and said motor to disconnect said power supply from said motor when excessive force is detected at said tubular cutter.

18. A specimen cutter comprising:

a housing;

a tubular specimen cutter mounted with respect to said housing to rotate on an axis through said tubular cutter;

a motor mounted with respect to said housing, said motor being connected to rotate said tubular cutter;

a power supply connected to said motor to rotate said cutter, said power supply having sufficient power to rotate said cutter a sufficient amount to cut a specimen; and an ejector rod positioned within said tubular cutter and there is an ejector motor connected to said ejector rod, an ejector switch connected to energize said ejector motor so that when a specimen is within said tubular cutter and said tubular cutter is positioned where it is desired that the specimen be ejected, said ejector switch can be actuated to actuate said ejector motor to cause said ejector rod to eject a specimen from said tubular cutter.

19. The specimen cutter of claim 18 wherein said ejector motor comprises a solenoid core connected to said ejector rod and a solenoid positioned to magnetically couple with said core to move said core and said ejector rod in a specimen ejecting direction.

* * * * *